(12) United States Patent
Hiles

(10) Patent No.: US 9,381,306 B2
(45) Date of Patent: Jul. 5, 2016

(54) DRIVE MECHANISM FOR A DRUG DELIVERY DEVICE AND DRUG DELIVERY DEVICE

(75) Inventor: John Hiles, South Wirral (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 859 days.

(21) Appl. No.: 13/702,823

(22) PCT Filed: Jun. 9, 2011

(86) PCT No.: PCT/EP2011/059577
§ 371 (c)(1),
(2), (4) Date: Feb. 8, 2013

(87) PCT Pub. No.: WO2011/154491
PCT Pub. Date: Dec. 15, 2011

(65) Prior Publication Data
US 2013/0131605 A1  May 23, 2013

(30) Foreign Application Priority Data

Jun. 11, 2010 (EP) .................................. 10165649

(51) Int. Cl.
*A61M 5/00* (2006.01)
*A61M 5/315* (2006.01)
*A61M 5/24* (2006.01)

(52) U.S. Cl.
CPC ....... *A61M 5/31551* (2013.01); *A61M 5/31543* (2013.01); *A61M 5/31555* (2013.01); *A61M 5/31585* (2013.01); *A61M 5/24* (2013.01)

(58) Field of Classification Search
CPC .............. A61M 5/24; A61M 5/31543; A61M 5/31555; A61M 5/31585; A61M 5/31576; A61M 5/31578; A61M 5/315

USPC .................. 604/187, 189, 207, 208, 209, 210
See application file for complete search history.

(56) References Cited

U.S. PATENT DOCUMENTS

2004/0236285 A1* 11/2004 Fisher ................. A61M 5/3158
604/207

FOREIGN PATENT DOCUMENTS

| WO | 01/72361 | 10/2001 |
|---|---|---|
| WO | 02/092153 | 11/2002 |

(Continued)

OTHER PUBLICATIONS

International Search Report for Int. App. No. PCT/EP2011/059577, completed Jul. 5, 2011.

(Continued)

*Primary Examiner* — Theodore Stigell
*Assistant Examiner* — Tiffany Legette
(74) *Attorney, Agent, or Firm* — McDonnell Boehnen Hulbert & Berghoff LLP

(57) ABSTRACT

A drive member and a rotation member are rotatable with respect to a housing. The drive member comprises drive fingers, which are resilient or resiliently mounted. A slider is disposed at the drive member and is axially movable between a first position, in which the slider keeps the drive fingers constrained, and a second position, in which the drive fingers are released. A unidirectional rotational clutch engages the drive member with the rotation member. The clutch is formed by the drive fingers when the slider is in the first position. The drive member and the rotation member are disengaged when the slider is in the second position. The slider is in the first position when a unit is attached to the housing, and in the second position when the unit is removed.

11 Claims, 7 Drawing Sheets

(56) References Cited

FOREIGN PATENT DOCUMENTS

| | | |
|---|---|---|
| WO | 03/008023 | 1/2003 |
| WO | 2009/049885 | 4/2009 |

OTHER PUBLICATIONS

International Preliminary Report on Patentability for Int. App. No. PCT/EP2011/059577, mailed Dec. 27, 2012.

\* cited by examiner

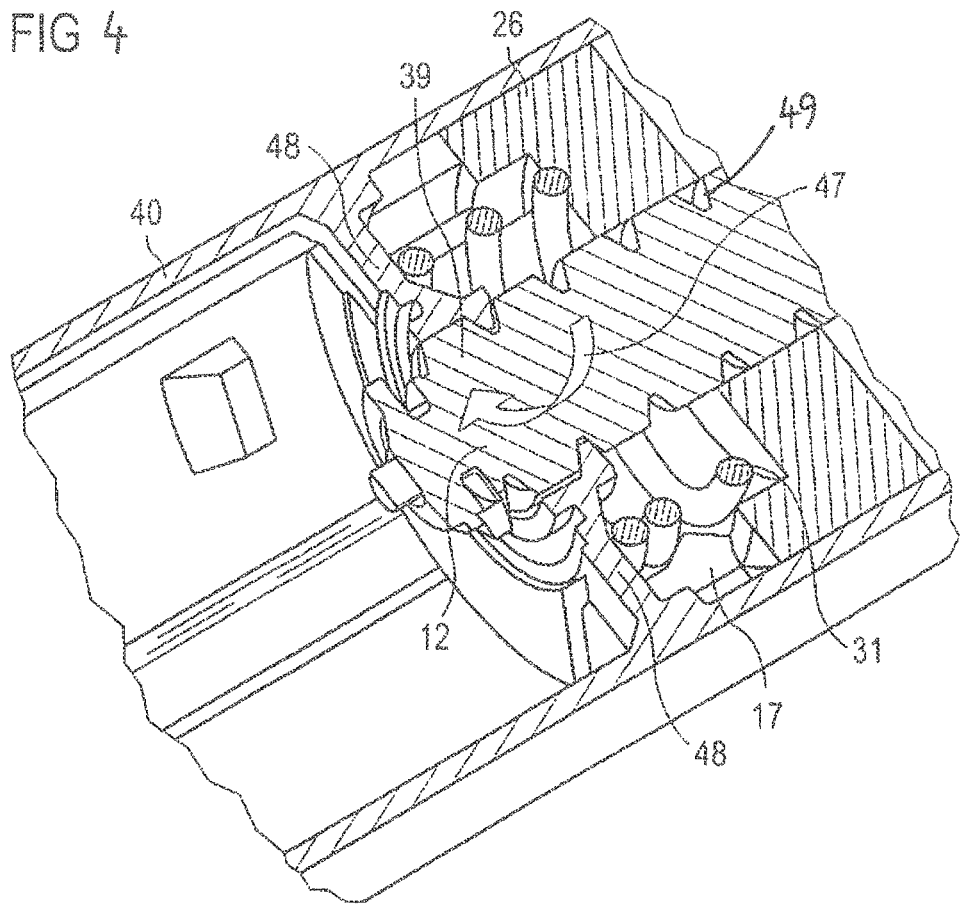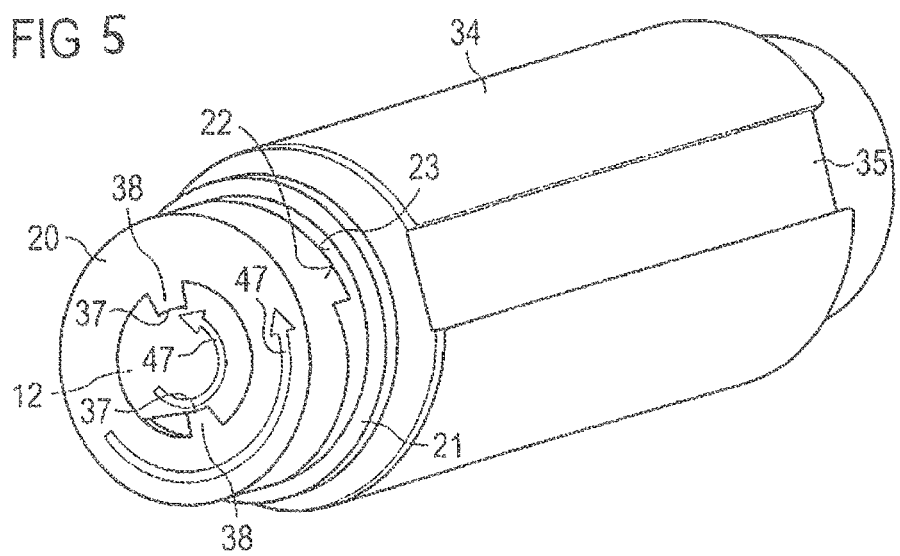

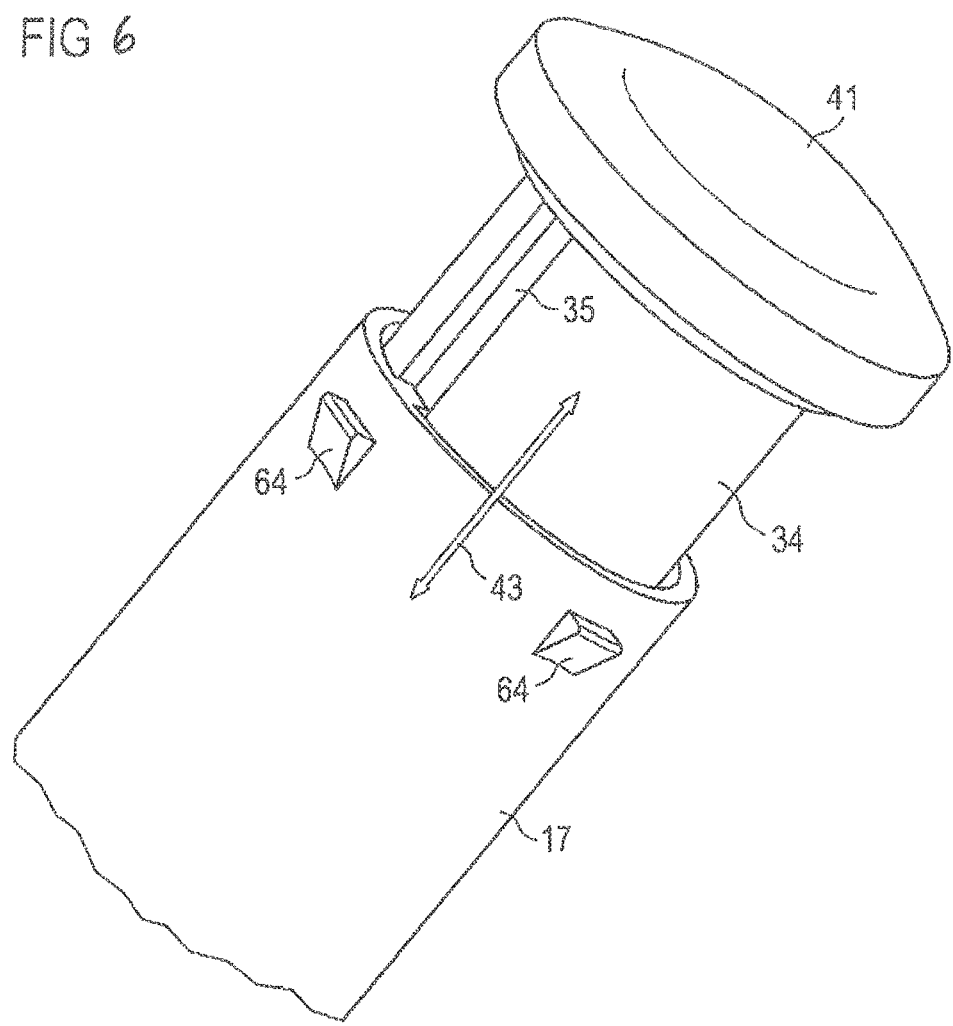

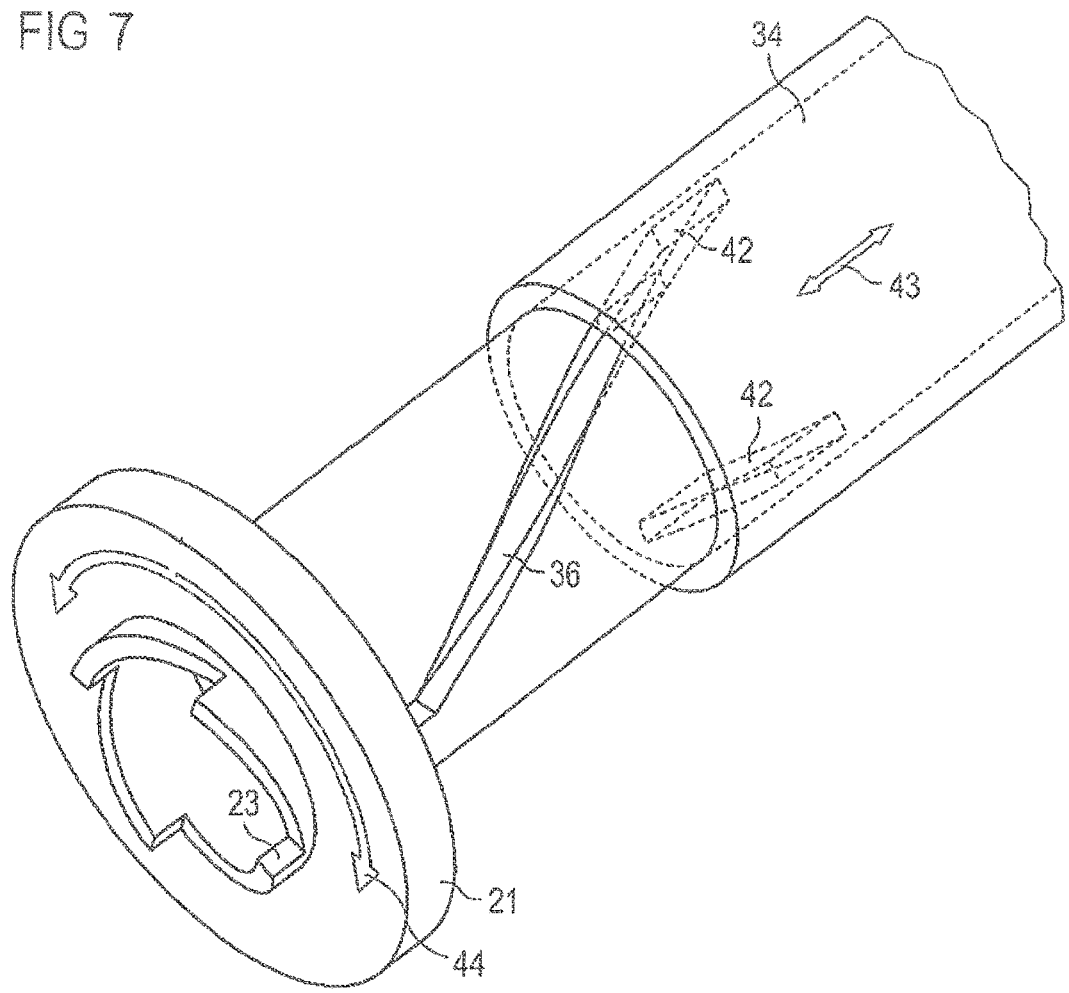

DRIVE MECHANISM FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. §371 of International Application No. PCT/EP2011/059577 filed Jun. 9, 2011, which claims priority to European Patent Application No. 10165649.4 filed on Jun. 11, 2010. The entire disclosure contents of these applications are herewith incorporated by reference into the present application.

FIELD OF INVENTION

The present invention relates to a resettable drive mechanism for a drug delivery device and a drug delivery device comprising such a drive mechanism.

BACKGROUND

In a drug delivery device, a piston within a cartridge that contains drug may be displaced with respect to the cartridge in the distal direction by a piston rod which moves in the distal direction with respect to the cartridge. Thereby, a dose of drug can be expelled from the cartridge. In order to provide for a reusable device, after the cartridge containing the drug has been emptied, the piston rod often has to be moved back from a distal end position to a proximal starting position.

WO 2009/049885 A1 describes an injection device which can be reset by removing the cartridge and thus disengaging the toothings of a steering element and a cylindrical sleeve, so that the piston rod can freely rotate.

WO 01/72361 A1 describes a one-way clutch means for use in an incrementing mechanism suitable for use in a medical injector device.

WO 02/092153 A2 describes a medication injector apparatus with a resettable cartridge plunger drive assembly including an axially floating nut, a cartridge plunger engaging screw, and a drive clutch movable with the nut.

WO 03/008023 A1 describes a medication dispensing apparatus having a manually operable plunger axially shiftable relative to the apparatus housing. A priming mechanism is operated by rotating an externally accessible driver portion.

SUMMARY

It is an object of the invention to disclose a drive mechanism and a drug delivery device offering an easy reset operation.

This object is achieved with a drive mechanism according to claim 1 and with a drug delivery device according to claim 10. Embodiments derive from the dependent claims.

The drive mechanism for a drug delivery device comprises a housing, a unit which is attachable to the housing and removable from the housing, and a drive member, a rotation member and a slider, which are arranged inside the housing. The drive member and the rotation member are rotatable with respect to the housing. The drive member comprises drive fingers, which are resilient or resiliently mounted. The slider is disposed at the drive member and is axially movable between a first position, in which the slider keeps the drive fingers constrained, and a second position, in which the drive fingers are released. A unidirectional rotational clutch engages the drive member with the rotation member. The clutch is formed by the drive fingers when the slider is in the first position. The drive member and the rotation member are disengaged when the slider is in the second position. The slider is in the first position when the unit is attached to the housing, and in the second position when the unit is removed from the housing.

In an embodiment of the drive mechanism the unit comprises a cartridge retaining member. When the cartridge retaining member is detached, a cartridge containing a drug can be inserted in the cartridge retaining member. The cartridge retaining member is attached, and the drug can be delivered by means of the drive mechanism. When the cartridge is empty, the cartridge retaining member is detached and the empty cartridge can be substituted with a new one.

In a further embodiment of the drive mechanism a removal of the unit allows a reset of a piston rod, which is coupled, preferably rotationally coupled, to the drive member.

A further embodiment of the drive mechanism comprises a stop member rotationally locked with respect to the housing or forming part of the housing. The stop member may especially be provided with a guide feature that prevents a rotation of the stop member with respect to the housing. A further unidirectional rotational clutch engages the stop member with the drive member when the slider is in the first position.

In a further embodiment of the drive mechanism the drive member is arranged between the rotation member and the stop member.

A further embodiment of the drive mechanism comprises a resilient member, which tends to hold the stop member in contact with the drive member and with a contact face of the slider and to hold the drive member in contact with the rotation member.

In a further embodiment of the drive mechanism the stop member is disengaged from the drive member when the slider is in the second position.

In a further embodiment of the drive mechanism the unit, in particular an insert sleeve of the unit, acts on the slider, in particular on a coupling sleeve of the slider, and keeps the slider in the first position when the unit is attached to the housing.

In a further embodiment of the drive mechanism the slider is a sleeve, and a taper is formed as part of the slider. The taper may have a conical shape. The drive fingers are splayed apart and thus disengaged from the rotation member by means of the taper when the slider is moved from the first position to the second position.

In a further embodiment of the drive mechanism the slider surrounds the drive member, and the taper is formed by an inner wall of the slider. The taper widens towards the rotation member. The drive fingers are located at an outer circumference of the drive member, which is arranged with the drive fingers extending towards the rotation member. The drive fingers are splayed apart and thus disengaged from the rotation member when the slider is moved from the first position to the second position.

In a further embodiment of the drive mechanism the drive fingers act on the slider in such a manner that the slider is moved from the first position to the second position when the unit is being removed from the housing.

A drug delivery device may comprise a drive mechanism according to the invention. The drug delivery device may be an injection device, particularly a pen-type injector. The drive mechanism may be provided for setting and delivering a fixed dose. The device may be a manually, in particular a non-electrically, operated device. The drug delivery device may additionally comprise a cartridge for holding a drug. The cartridge may be inserted in a unit provided as a cartridge holder or cartridge retaining member, which may be releasably attached to the housing.

The housing or a drug delivery device comprising the housing has a distal end and a proximal end. The term "distal end" designates that end of the housing, the device or a component thereof which is or is to be arranged closest to a dispensing end of the device. The term "proximal end" designates that end of the housing, the device or a component thereof which is or is to be arranged furthest away from the dispensing end of the device. Accordingly, the "distal direction" is the direction from the proximal end towards the distal end, and the "proximal direction" is the direction from the distal end towards the proximal end.

The term "drug", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

A resettable drive mechanism for a drug delivery device preferably comprises a housing with a proximal end and a distal end, the drive member being rotatable with respect to the housing in a second direction for delivering a dose of a drug, the piston rod being adapted to be driven in a distal direction with respect to the housing by the drive member, when the drive member rotates in the second direction, a stop member being adapted to prevent rotation of the drive member in a first direction opposite to the second direction with respect to the housing, when the stop member engages the drive member, and a clutch member movable with respect to the housing between a delivery position and a reset position.

When the clutch member is in the delivery position, the stop member and the drive member are engaged, and the drive member is prevented from rotating in the first direction with respect to the housing. When the clutch member is in the reset position, the drive member and the stop member are disengaged, the drive member is rotatable in the first direction with respect to the housing and the piston rod is movable in the proximal direction with respect to the housing.

The clutch member may be (linearly) displaced with respect to the housing when the clutch member is moved from the delivery position into the reset position or from the reset position into the delivery position. The clutch member may be displaced with respect to one of the drive member and the stop member when the clutch member is moved from the delivery position into the reset position or from the reset position into the delivery position. The other one of the drive member and the stop member may follow movement of the clutch member when the clutch member is moved from the delivery position into the reset position or from the reset position into the delivery position. Via this relative movement, drive member and stop member may be disengaged. The clutch member may be axially displaced with respect to the housing when it is moved from the delivery into the reset position and preferably when it is moved from the delivery position into the reset position. The clutch member may be secured against rotational movement with respect to the housing.

If a clutch member that is movable with respect to the housing between the delivery position and the reset position is provided, a movement of the piston rod in the proximal direction with respect to the housing is facilitated. In particular, since the drive member may be rotated in the first direction with respect to the housing, the drive member may rotate in that direction which is opposite to the one during delivery of the dose of drug without the rotational movement in the first direction being prevented by the stop member. Thus, proximal movement of the piston rod which may cause the drive member to be rotated in the first direction is no longer prevented and resetting of the drive mechanism is facilitated.

The stop member and the drive member may be permanently engaged while the clutch member is in delivery position. The drive member may engage the piston rod. The drive member may be permanently engaged with the piston rod regardless whether the clutch member is in delivery position or in the reset position.

Rotational movement of the drive member may be converted into rotational movement of the piston rod in the same direction. Rotational movement of the piston rod may be converted into displacement of the piston rod with respect to the housing in the distal direction, for example by a threaded engagement of the piston rod with the housing. The piston rod may be displaced in the distal direction with respect to the housing and rotate in the second direction during the distal displacement. The piston rod may be displaced along its rotation axis.

Alternatively, a rotational movement of the drive member may be converted into pure (linear) displacement of the piston rod with respect to the housing. Thus, the piston rod may move translationally with respect to the housing without rotating. A displacement axis of the piston rod may run transversely with respect to the rotation axis around which the drive member rotates.

In an embodiment of the drive mechanism the clutch comprises a resilient member, which may be a spring. The clutch resilient member may be biased when the clutch member is in the delivery position. The clutch resilient member may be fully or partly relaxed when the clutch member is in the reset position.

In another embodiment, the drive mechanism comprises a clutch stop member. The clutch stop member may be movable with respect to the clutch member. The clutch stop member may be removable, in particular from the drive mechanism. The clutch stop member may be arranged to keep, preferably to hold, the clutch member in the delivery position. The clutch stop member may be provided for preventing movement of the clutch member towards the reset position. The clutch stop member may be arranged to counteract the force exerted by the clutch resilient member that tends to move the clutch member in the reset position. The clutch stop member is preferably releasably secured with respect to the housing. If the clutch stop member is removed from the clutch member, e.g. detached from the housing, the clutch member is permitted to move into the reset position after the clutch stop member has been removed. Thus, the clutch stop member may keep the drive mechanism in a delivery state by preventing movement of the clutch member towards the reset position. If the clutch stop member is removed from the clutch member, the clutch member may be moved into the reset position, which movement puts the drive mechanism in a reset state.

The clutch stop member and the clutch resilient member, in combination, may also be provided for an automatically actuated reset mechanism of the drive mechanism. Due to the biased clutch resilient member, the clutch member is moved automatically into a reset position when the clutch stop member is removed.

The rotation member may be adapted to be rotated in the first direction with respect to the housing during setting of a dose of a drug and to be rotated in the second direction with respect to the housing during delivery of the dose. Rotation of the rotation member in the second direction with respect to the housing may be converted into rotation of the drive member in the second direction with respect to the housing, e.g. by mechanical cooperation of the rotation member and the drive member. Rotation of the drive member may be converted into movement of the piston rod with respect to the housing, e.g. by mechanical cooperation of drive member and piston rod and preferably additionally by mechanical cooperation of piston rod and housing, e.g. by a threaded engagement.

According to another embodiment, the drive member, preferably permanently, abuts and/or engages one of or both of stop member and rotation member during (rotational) movement of the rotation member for setting and delivery of the dose. Thus, when the clutch member is in the delivery position, the drive member may, preferably permanently, abut one of or both of rotation member and stop member. The drive member may be coupled to the stop member and/or rotation member during setting and delivery of the dose.

In another embodiment, the drive mechanism comprises a resilient member, which may be a spring. The resilient member may be arranged to keep the stop member and the drive member in abutment and/or engagement. The resilient member may exert a force on one of or both of the drive member and the stop member which force tends to keep the drive member and the stop member in engagement. Preferably, this force has to be overcome for disengaging drive member and stop member.

In another embodiment, the clutch resilient member is a clutch spring member and the resilient member is a spring member. The clutch spring member preferably has a spring strength which is greater than a spring strength of the spring member. Thus, the clutch resilient member may exert a force on the clutch member which overcomes the force exerted by the resilient member by which the stop member and the drive member are kept in abutment and/or engagement. Accordingly, disengaging stop member and drive member is facilitated.

In another embodiment, the stop member and the drive member are arranged to be moved into engagement when the clutch member is moved from the reset position towards the delivery position. The force exerted by the resilient member may assist this movement. An additional external force may be applied for (re-)engaging stop member and drive member. It may be necessary to overcome the force exerted by the clutch resilient member for (re-)engaging stop member and drive member.

In another embodiment, the drive member and the stop member are engaged to form a unidirectional friction clutch mechanism when the clutch member is in the delivery position. Accordingly, relative rotational movement of the drive member with respect to the stop member and, in particular, with respect to the housing in the first direction is prevented when the clutch member is in the delivery position. When the clutch member is in the reset position, the unidirectional clutch is open. Thus, when the clutch member is in the reset position, relative rotational movement between drive member and stop member in the first rotational direction is expediently allowed.

In another embodiment, the drive member and the rotation member are engaged to form a (further) unidirectional friction clutch mechanism when the clutch member is in the delivery position and, preferably, also when the clutch member is in the reset position. This mechanism is expediently configured to prevent relative rotational movement between drive member and rotation member in the second direction.

In another embodiment, the stop member is secured against rotational movement with respect to the housing and the stop member is displaceable with respect to the housing.

In another embodiment, the stop member is arranged to follow movement of the clutch member towards the reset position, thereby disengaging from the drive member.

In another embodiment, the clutch member is arranged to abut the stop member when the clutch member is moved towards the reset position. Preferably, the clutch member carries the stop member with it towards the reset position after having moved into abutment with the stop member.

In an embodiment of a drug delivery device comprising a drive mechanism as described, the cartridge or a cartridge retaining member, which is adapted to retain and/or attach the cartridge to the housing, is the clutch stop member. Thus, the cartridge or the cartridge retaining member may prevent the clutch member from moving into the reset position on account of the force exerted by the clutch resilient member. If the cartridge retaining member or the cartridge is detached from the housing, the clutch member will automatically move into reset position.

Further objects, features and advantages of the invention will become apparent from the following detailed description in conjunction with the appended drawings.

BRIEF DESCRIPTION OF THE FIGURES

FIG. 4 shows a further detail of an embodiment of the drive mechanism including a stop member.

FIG. 5 shows a further detail of an embodiment of the drive mechanism including a rotation member.

FIG. 6 shows a further detail of an embodiment of the drive mechanism including a dose member.

FIG. 7 shows a further detail of an embodiment of the drive mechanism including an engagement between the rotation member and the dose member.

Like elements, elements of the same kind and identically acting elements carry the same reference numerals.

DETAILED DESCRIPTION

Figure 1:
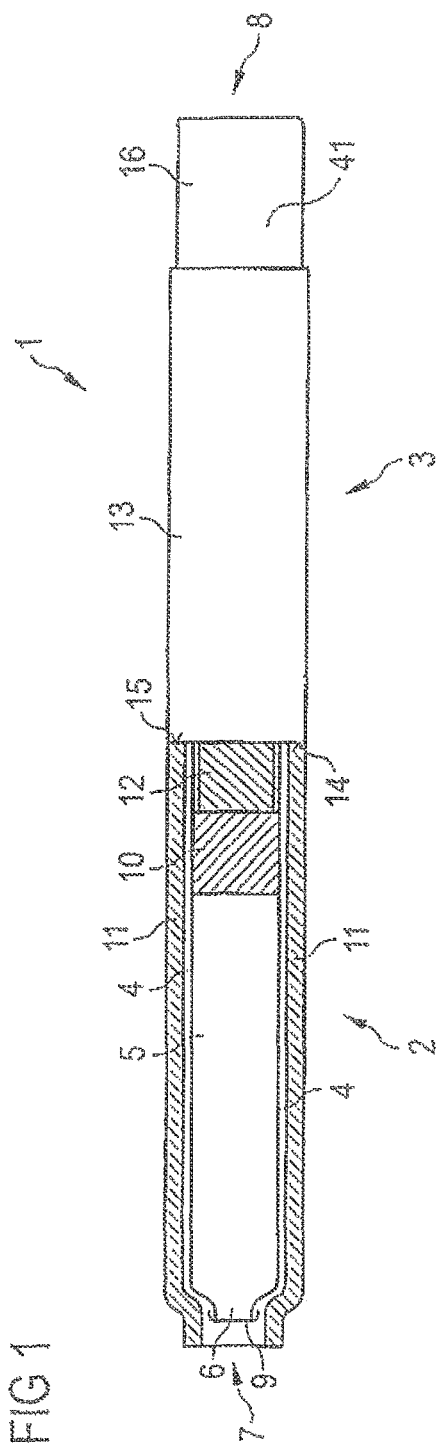
FIG. 1 schematically shows a partly sectional side view of an embodiment of a drug delivery device.
Figure 2:
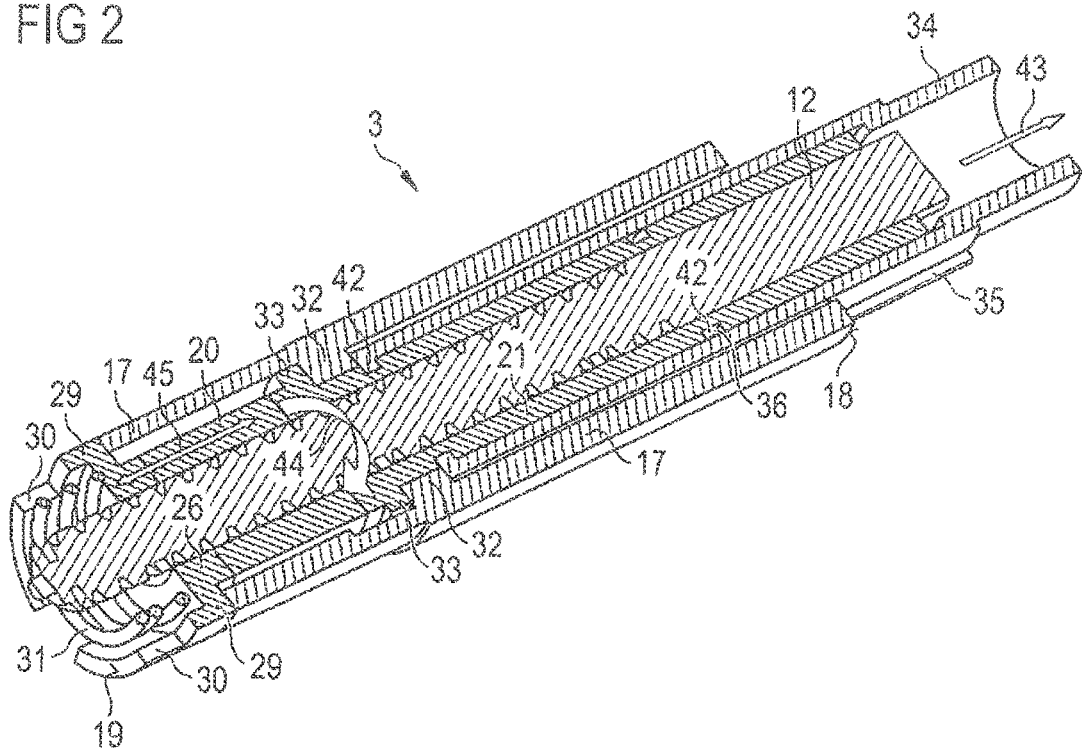
FIG. 2 shows a perspective view of a cross-section of a drive mechanism.

FIG. 1 shows a drug delivery device 1 having a distal end 7 and a proximal end 8 and comprising a cartridge unit 2 and a drive unit 3. The cartridge unit 2 comprises a cartridge 4. Drug 5 is retained in the cartridge 4. The drug 5 is preferably liquid drug. The cartridge 4 preferably comprises a plurality of doses of the drug 5. The drug 5 may comprise insulin, heparin, or growth hormones, for example. The cartridge 4 has an outlet 6 at its distal end. Drug 5 can be dispensed from the cartridge through outlet 6. The device 1 may be a pen-type device, in particular a pen-type injector. The device 1 may be a disposable or a reusable device. The device 1 may be a device configured to dispense fixed doses of the drug. The device 1 may be a needle-based or a needle free device. The device 1 may be an injection device.

The outlet 6 may be covered by a membrane 9, which protects drug 5 against external influences during storage of the cartridge. For drug delivery, membrane 9 may be opened, e.g. pierced. For example, membrane 9 may be pierced by a needle unit (not explicitly shown). The needle unit may be (releasably) attached to the distal end of the cartridge unit 2. The needle unit may provide for fluid communication from the inside of the cartridge 4 to the outside of the cartridge through outlet 6.

A piston 10 is retained within the cartridge 4. The piston 10 is movable with respect to the cartridge. The piston 10 may seal the drug 5 within the cartridge. The piston 10 expediently seals the interior of the cartridge 4 proximally. Movement of the piston 10 with respect to the cartridge 4 in the distal direction causes drug 5 to be dispensed from the cartridge through outlet 6 during operation of the device.

The cartridge unit 2 furthermore comprises a cartridge retaining member 11. The cartridge 4 is retained within the cartridge retaining member 11. The cartridge retaining member 11 may stabilize the cartridge 4 mechanically. Additionally or alternatively, the cartridge retaining member 11 may be provided with a fixing member (not explicitly shown) for attaching the cartridge unit 2 to the drive unit 3.

The cartridge unit 2 and the drive unit 3 are secured to one another, preferably releasably secured. A cartridge unit 2 which is releasably secured to the drive unit may be detached from the drive unit 3, for example in order to allow for providing for a new cartridge 4, if all of the doses of drug which once were in the cartridge formerly attached to the drive unit 3 have already been dispensed. The cartridge retaining member 11 may be releasably secured to the drive unit 3 via a thread, for example.

Alternatively, the cartridge retaining member 11 may be dispensed with. It is particularly expedient, in this case, to apply a robust cartridge 4 and to attach the cartridge directly to the drive unit 3.

The drive unit 3 is configured for transferring force, preferably user-exerted force, particularly preferably manually exerted force, to the piston 10 for displacing the piston 10 with respect to the cartridge 4 in the distal direction. A dose of drug may be dispensed from the cartridge in this way. The size of the delivered dose may be determined by the distance by which the piston 10 is displaced with respect to the cartridge 4 in the distal direction.

The drive unit 3 comprises a drive mechanism. The drive mechanism comprises a piston rod 12. The piston rod 12 may be configured for transferring force to the piston 10, thereby displacing the piston in the distal direction with respect to the cartridge 4. A distal end face of the piston rod 12 may be arranged to abut a proximal end face of the piston 10. A bearing member (not explicitly shown) may be arranged to advance the piston 10, preferably to abut the proximal end face of the piston 10. The bearing member may be arranged between piston 10 and piston rod 12. The bearing member may be fixed to the piston rod 12 or a separate member. If the piston rod 12 is configured to be rotated during operation of the device, for example during dose delivery, it is particularly expedient to provide for a bearing member. The bearing member may be displaced together with the (rotating) piston rod with respect to the housing. The piston rod may be rotatable with respect to the bearing member. In this way, the risk that the rotating piston rod drills into the piston and thereby damages the piston is reduced. Accordingly, while the piston rod rotates and is displaced with respect to the housing, the bearing member is preferably only displaced, i.e. does not rotate. The piston rod may be bounded by the bearing member.

The drive unit 3 comprises a housing 13 which may be part of the drive mechanism. The piston rod 12 may be retained in the housing. A proximal end side 14 of the cartridge unit 2 may be secured to the drive unit 3 at a distal end side 15 of the housing 13, for example via a threaded connection. Housing 13, cartridge 4 and/or cartridge retaining member 11 may have a tubular shape.

The term "housing" shall preferably mean any exterior housing ("main housing", "body", "shell") or interior housing ("insert", "inner body") which may have a unidirectional axial coupling to prevent proximal movement of specific components. The housing may be designed to enable the safe, correct, and comfortable handling of the drug delivery device or any of its mechanism. Usually, it is designed to house, fix, protect, guide, and/or engage with any of the inner components of the drug delivery device (e.g., the drive mechanism, cartridge, piston, piston rod), preferably by limiting the exposure to contaminants, such as liquid, dust, dirt etc. In general, the housing may be unitary or a multipart component of tubular or non-tubular shape.

The term "piston rod" shall preferably mean a component adapted to operate through/within the housing, which may be designed to transfer axial movement through/within the drug delivery device, preferably from the drive member to the piston, for example for the purpose of discharging/dispensing an injectable product. Said piston rod may be flexible or not. It may be a simple rod, a lead-screw, a rack and pinion system, a worm gear system, or the like. "piston rod" shall further mean a component having a circular or non-circular cross-section. It may be made of any suitable material known by a person skilled in the art and may be of unitary or multipart construction.

The drive unit 3 comprises a dose part 16. The dose part 16 is movable with respect to the housing 13. The dose part 16 may be movable in the proximal direction with respect to the housing for setting of a dose of the drug 5 which is to be delivered and in the distal direction with respect to the housing for delivery of the set dose. The dose part 16 is preferably connected to the housing 13. The dose part 16 may be secured against rotational movement with respect to the housing. The dose part 16 may be moved (displaced) between a proximal end position and a distal end position with respect to the housing 13 (not explicitly shown). The distance by which the dose part is displaced with respect to the housing during setting of the dose may determine a size of the dose. The proximal end position and the distal end position may be determined by a respective stop feature which may limit the proximal or distal travel of a dose member with respect to the housing.

The device 1 may be a manually, in particular non-electrically, driven device. The (user-applied) force which causes the dose part 16 to be moved with respect to the housing 13 in the distal direction may be transferred to the piston rod 12 by the drive mechanism. For this purpose, other elements of the drive mechanism may be provided which are not explicitly shown in FIG. 1. When the dose part is moved in the proximal direction with respect to the housing for setting a dose, a movement of the piston rod 12 with respect to the housing 13 is preferably prevented.

Embodiments of a drive mechanism which are suitable to be provided in the drug delivery device 1 as it was described above are described in more detail below.

Embodiments of a drive mechanism which is suitable for being implemented in the drug delivery device 1 as described above are described in connection with FIGS. 2 to 7.

The drive mechanism comprises a housing part 17. The housing part 17 has a proximal end 18 and a distal end 19. The housing part 17 may be (outer) housing 13 of FIG. 1, a part thereof or an insert within housing 13, which insert is preferably secured against rotational and axial movement with respect to housing 13. The housing part 17 may be an insert sleeve, for example. The insert sleeve may be snap-fitted or glued to housing 13, for example. The housing part 17 may have a tubular shape. Housing part 17 may comprise outer fixing elements 64, for example snap-fit elements, for fixing housing part 17 to housing 13 (cf. FIG. 6).

The piston rod 12 is retained in the housing 13, preferably within housing part 17. The piston rod 12 is driven in the distal direction with respect to the housing part 17 during dose delivery.

The drive mechanism furthermore comprises a drive member 20. Drive member 20 is retained within the housing part 17. Drive member 20 is configured to transfer force, preferably torque, to the piston rod 12. The transferred force may cause the piston rod 12 to be displaced in the distal direction with respect to the housing part 17 for dose delivery.

Drive member 20 is rotatable with respect to housing part 17. The drive member 20 may engage the piston rod 12. Rotational movement of the drive member, for example rotational movement in a second direction may be converted into distal movement of the piston rod 12 with respect to the housing part 17. This is explained in more detail below.

The drive mechanism furthermore comprises a rotation member 21. The rotation member 21 is rotatable with respect to the housing part 17 in a first direction, in particular for setting of a dose of the drug, and in a second direction, in particular for delivering the set dose. The second direction is opposite to the first direction. The first direction may be counter-clockwise and the second direction may be clockwise as seen from the proximal end of the device, for example.

Drive member, rotation member and/or piston rod are preferably configured to be rotatable about a (common) rotation axis. The rotation axis may extend through drive member, rotation member and/or piston rod. The rotation axis may be the main longitudinal axis of the piston rod. The rotation axis may run between the proximal end and the distal end of the housing part 17.

The rotation member 21 is coupled to the drive member 20 by an uni-directional clutch mechanism, in particular a friction clutch mechanism. This clutch mechanism permits rotational movement of the rotation member 21 with respect to the drive member 20 when the rotation member rotates in the first direction with respect to the housing part 17. The clutch mechanism prevents rotational movement of the rotation member 21 with respect to the drive member 20, when the rotation member rotates in the second direction with respect to the housing part 17. The drive member 20 may thus follow rotational movement of the rotation member 21 in the second direction with respect to the housing part 17.

The drive member 20 is arranged to abut and/or engage the rotation member and, in particular, engages rotation member 21. The drive member 20 comprises a toothing 22. Toothing 22 may be provided at one end of the drive member, e.g. its proximal end. The rotation member comprises a toothing 23. Toothings 22 and 23 face one another. Toothing 23 may be provided at one end of the rotation member which end faces the drive member 20, e.g. at the distal end of the rotation member. Toothing 22 comprises a plurality of teeth 24. Toothing 23 comprises a plurality of teeth 25. Teeth 24 and/or 25 may extend and preferably may be oriented along the rotation axis. Toothings 22 and 23 may be configured to mate with one another. The rotation member and the drive member may engage each other by toothings 22 and 23 being in engagement.

The teeth 24 and/or teeth 25 may be ramp-shaped, in particular along the azimuthal (angular) direction as seen from the rotation axis. The ramp of the respective tooth is limited (in the angular direction) by a steep end face of that tooth, i.e. a face of the tooth that runs parallel to the rotation axis or includes a smaller angle with the rotation axis when projected on this axis than the ramp when projected on this axis. The steep end face is followed by the ramp of the next tooth.

The teeth 24 may be circumferentially disposed on the drive member 20, particularly at the end of the drive member 20 which faces the rotation member 21. The teeth 25 may be circumferentially disposed on the rotation member 21, particularly at the end of the rotation member 21 which faces the drive member 20.

When the steep end faces of two teeth abut and the rotation member is rotated further on in the second direction, the steep sides stay in abutment and drive member 20 follows the rotation of rotation member 21. When the rotation member rotates in the first direction, the ramp of the teeth—which ramps, in particular, run obliquely with respect to the rotation axis—slide along each other and, in consequence, the rotation member 21 may rotate with respect to the drive member 20.

The drive mechanism furthermore comprises a stop member 26. The drive member 20 may be arranged between the stop member 26 and the rotation member 21. The stop member 26 is configured for preventing rotational movement of the drive member 20 in the first direction with respect to the housing part 17 during setting of a dose, i.e. when the rotation member 21 rotates in the first direction. Thus, the rotation member 21 may rotate in the first direction with respect to the housing part 17, whereas the drive member 20 and the stop member 21 do not rotate.

The stop member 26 is coupled to the drive member 20 by another uni-directional clutch mechanism, in particular a friction clutch mechanism. This clutch mechanism prevents rotational movement of the drive member 20 with respect to the stop member 26 when the rotation member 21 rotates in the first direction with respect to the housing part 17. The clutch mechanism permits rotational movement of the drive member 20 with respect to the stop member 26, when the rotation member 21 rotates in the second direction with respect to the housing part 17.

Thus, the rotation member 21 may rotate with respect to the drive member 20 and the stop member 26 in the first direction during setting of the dose, with rotation of the drive member 20 being prevented by its interaction with the stop member 26, and rotation member 21 as well as drive member 20 may rotate with respect to the stop member 26 in the second direction during delivery of the dose.

The stop member may be arranged to abut and/or engage the drive member during setting of the dose and, preferably, during delivery of the dose. The stop member 26 is provided with teeth 27 on that side of the stop member 26 which faces the drive member 20. The teeth 27 may be ramp-shaped with a steep side and a less steep ramp. The teeth 27 may be azimuthally disposed along the stop member 26, in particular on the perimeter of the stop member 26. The teeth 27 may extend and preferably may be oriented along the rotation axis.

The drive member 20 is provided with teeth 28 on that side of the drive member 20 which faces the stop member 26. The teeth 28 may extend and preferably be oriented along the rotation axis. The teeth 24 and the teeth 28 of the drive member 20 are oppositely disposed. The teeth 24 may be configured corresponding to the teeth 25 of the rotation member 21. The teeth 28 may be configured corresponding to the teeth 27 of the stop member 26. The teeth 27 and 28 may face one another and may especially mate with one another. The teeth 27 and 28, in particular the steep sides of the teeth, cooperate, e.g. abut, for preventing rotation of the drive member 20 with respect to the housing part 17 and, in particular, with respect to the stop member 26 in the first direction.

Stop member 26 is preferably secured against rotational movement, particularly preferably permanently secured against rotational movement, with respect to the housing part 17. Stop member 26 may be fixed to the housing or integrated into the housing. Stop member 26 may be fixed against displacement with respect to the housing part 17 or displacement with respect to the housing part 17 may be allowed.

As it is illustrated in the present embodiment, stop member 26 is displaceable with respect to the housing but non-rotatable with respect to the housing part 17. For that purpose, one or a plurality of, preferably oppositely disposed, guide features, for example guide lugs 29, are provided in the stop member 26. The respective guide feature 29 engages a corresponding guide slot 30 which may be provided in the housing, e.g. in housing part 17. This can be seen in FIGS. 2 to 5. A guide feature 29 cooperates with a guide slot 30 to prevent rotational movement of the stop member with respect to the housing part 17, with axial movement of the stop member 26 with respect to the housing being allowed. The axial movement of the stop member 26 may compensate for play between components of the drive mechanism during operation.

From the group comprising the drive member 20, the stop member 26 and the rotation member 21 one or more members, preferably two members or three members, may be axially displaceable with respect to the housing part 17 and, preferably, with respect to the piston rod 12. Therein, the drive member and another one of the recited members may be axially displaceable with respect to the housing. The remaining member may be secured against axial displacement or may also be axially displaceable during operation of the drive mechanism for drug delivery. Accordingly, if the drive member and the stop member are axially displaceable, the rotation member may be axially secured or axially displaceable and so on. Play between the components caused by relative (axial) movement of components of the clutch mechanism with respect to the housing can be compensated for in this way. The distance by which the respective components may be axially displaced with respect to the housing may correspond to the (maximum) depth of a tooth of the respective toothing 22 or 28 of the drive member. Alternatively, the distance may be greater than the (maximum) depth of a tooth of the respective toothing.

Furthermore, the drive mechanism comprises a resilient member 31, preferably a spring member. The resilient member 31 may be biased during drug delivery operation of the drive mechanism. The resilient member may provide for a force that tends to keep the drive member 20 in engagement with the stop member 26 and/or the rotation member 21. The force may be exerted along the rotation axis. In the situation shown in FIGS. 2 and 3, this force may be exerted in the proximal direction. The resilient member 31 may be a helical (coil) spring. The resilient member 31 may be a compression spring.

The resilient member 31 may keep the drive member 20 and the stop member 26 in (permanent) mechanical contact, e.g. in abutment, with each other during setting and delivery of a dose of the drug. Alternatively or additionally, the resilient member 31 may keep the drive member 20 and the rotation member 26 in (permanent) mechanical contact, preferably abutment, with each other during setting and delivery of a dose of the drug.

The resilient member 31 may be integrated within stop member 26 or a separate component. The resilient member 31 may be arranged on the distal end side of the stop member 26.

The drive mechanism furthermore comprises a support member 32. Support member 32 is expediently fixed against axial and rotational movement with respect to the housing part 17 or integrated into housing part 17. Support member 32 is arranged on that side of the drive member 20 which is remote from the stop member 26. Support member 32 may be a protrusion, for example a ring-like protrusion. Rotation member 21 may extend through an opening in support member 32. The support member 32 may provide for a counter force to the force which is exerted by the resilient member 31. Permanent abutment of the rotation member with the drive member and of the drive member with the stop member during setting and delivery of drug is facilitated in this way.

The rotation member 21 has an (radially) outwardly protruding member 33, for example a flange portion. The protruding member 33 is expediently provided for abutting support member 32, in particular the distal end side of support member 32.

Another support 48 (cf. FIG. 4) may be provided for providing a counterforce to the force exerted by the resilient member 31. Support 48 is arranged on that side of the drive member 20 which is remote from the rotation member 21. Support 48 is arranged on that side of the stop member 26 which is remote from the support member 32. The support 48 may be arranged to abut the resilient member 31. The support 48 may be secured against axial and rotational movement with respect to the housing part 17, with respect to the housing 13 or integrated into the housing 13, for example into (additional) housing part 40 (cf. FIG. 4).

The drive mechanism furthermore comprises a dose member 34. Dose member 34 may be dose part 16 or may be a part of the dose part 16 of FIG. 1. Dose member 34 is movable with respect to the housing in the proximal direction for setting of a dose and for delivery of the dose. For example, the dose member 34 may be moved in the proximal direction with respect to the housing part 17 during dose setting and in the distal direction with respect to the housing part 17 during dose delivery. The dose member 34 may engage the housing part 17 or, alternatively, another part of housing 13 (not explicitly shown). Dose member 34 is preferably secured against rotational movement with respect to the housing part 17. The dose member 34 may comprise a guide feature 35, for example a guide lug or a guide slot, that engages another guide feature, for example a guide slot or a guide lug, respectively, that is provided in the housing part 17 or the housing 13. The dose member 34 may be displaced with respect to housing part 17 preferably only axially along and/or rotationally around the rotation axis.

Dose member 34 may be moved in the proximal direction and in the distal direction with respect to rotation member 21. Dose member 34 is arranged to be coupleable and is preferably (permanently) coupled to rotation member 21 such that movement of the dose member, e.g. in the proximal direction with respect to the housing part 17, for setting a dose of the drug is converted into rotational movement of the rotation member in the first direction and movement of the dose member, e.g. in the distal direction with respect to the housing part 17, for delivering the dose is converted into rotational movement of the rotation member 21 in the second direction opposite to the first direction.

The rotation member 21 may be arranged inside the dose member 34, or the dose member 34 may be arranged inside the rotation member 21. If the rotation member 21 is arranged inside the dose member 34, the rotation member 21 may be provided with an (outer) thread 36, which may be engaged with an engagement member 42 or with a plurality of engagement members 42 of the dose member 34, preferably on an inner wall of the dose member 34. The engagement member 42 may be a lug or a thread or a part of a thread, for example. If the dose member 34 is arranged inside the rotation member 21, the dose member 34 may be provided with an (outer) thread, which may be engaged with an engagement member or with a plurality of engagement members of the rotation member 21, preferably on an inner wall of the rotation member 21. Thus, dose member 34 and rotation member 21 may be threadedly coupled, in particularly threadedly engaged.

The rotation member 21, the drive member 20, the stop member 26 and/or the dose member 34 may be or may comprise a respective sleeve. The piston rod 12 may be arranged to be driven and, in particular, may be driven through one of, more of or all of those sleeves. The piston rod 12 may run through one of, more of or all of those sleeves.

The drive member 20 and the piston rod 12 are configured for rotational movement of the drive member 20 with respect to the housing being converted into rotational movement of the piston rod with respect to the housing. The drive member 20 may engage the piston rod 12. The piston rod 12 is displaceable with respect to the drive member 20 along a displacement axis, which is parallel to the rotation axis. The drive member 20 may be splined to the piston rod 12, for example.

The piston rod 12 is threadedly coupled to the housing 13. The piston rod 12 may be provided with an outer thread 49, for example. The piston rod 12 may extend through and be engaged with a (part) thread in opening 39 which is provided in housing part 40, for example in support 48 (cf. FIG. 4). Housing part 40 may be formed integrally with housing part 17, may be a housing part fixed thereto or may be a housing part secured separately from housing part 17 to housing 13.

The piston rod 12 comprises an engagement track 37, preferably two oppositely disposed engagement tracks, on the outside. The (respective) engagement track 37 may interrupt thread 49. The (respective) engagement track 37 preferably extends along the axis along which the piston rod is displaceable with respect to the housing and, in particular, with respect to the drive member.

Rotational movement of the drive member 20 with respect to the housing may thus be converted into rotational movement of the piston rod 12 with respect to the housing and the rotational movement of the piston rod 12 is, on account of the threaded engagement of the piston rod and the housing (part), converted into movement of the piston rod with respect to the housing in the distal direction.

The dose part 16 (cf. FIG. 1) may comprise a dose button 41 (cf. FIG. 6). Dose button 41 may be configured to be gripped by a user. Dose button 41 may be arranged and connected to the dose member 34 at the proximal end. Dose button and dose member may be unitary.

The operation of the drive mechanism will be described in the following. To set a dose, dose member 34 is moved in the proximal direction (arrow 43 in FIG. 2) with respect to the housing part 17 (first type of movement). To do so, the user may grip dose button 41 and pull it in the proximal direction. Dose member 34 moves proximally also with respect to the rotation member 21. Proximal movement of the rotation member is prevented by support member 32 which abuts protruding member 33 of rotation member 21. Consequently, the proximal movement of dose member 34 with respect to the housing part 17 is converted into rotational movement of the rotation member 21 in the first direction (arrow 44 in FIG. 2) with respect to the housing part 17, in particular on account of the engagement of dose member 34 and rotation member 21. Thus, the rotation member 21 rotates in the first direction with respect to the housing, which in the present embodiment is counter-clockwise as seen from the proximal end of the rotation member 21. The rotation member 21 also rotates with respect to the drive member 20 and to the stop member 26. The drive member 20 is prevented from rotating in the first direction by interaction with the stop member 26, e.g. by interlocking of teeth 27 and 28. As the piston rod 12 is coupled to the drive member 20 and rotation in the first direction of the drive member would cause the piston rod to travel in the proximal direction, the piston rod 12 is prevented from being driven in the proximal direction by interaction of stop member 26 and drive member 20. By preventing the piston rod 12 from moving during dose setting dose accuracy can be increased.

When the rotation member 21 rotates in the first direction, the ramps of the teeth 25 of the rotation member 21 slide along the ramps of the teeth 24 of the drive member 20. Thus, the teeth 25 of the rotation member 21 turn around the rotation axis until they engage the next teeth of the drive member 20. During this movement, the drive member 20 and, in particular, the stop member 26 are displaced along the rotation axis with respect to piston rod 12 and housing by a distance determined by, preferably equal to, the depth of a tooth. When the teeth of the rotation member 21 engage the next teeth of the drive member 20, the force exerted by the resilient member 31 moves the drive member 20 and, in particular, the stop member 26 back along the rotation axis into the axial start position. An according movement of the stop member 26 and the drive member 20 in the distal direction and back into the proximal direction is indicated by the double arrow 45 in FIGS. 2 and 3. A tooth of the rotation member which engages the next tooth of the drive member may cause an audible and/or tactile feedback to the user.

The drive mechanism is especially suitable for a fixed-dose device. The size of the fixed dose of drug which is to be delivered is preferably determined by the distribution of the teeth of the respective toothings in the drive member, rotation member and stop member. The rotation member 21 may especially have to be rotated over only one tooth of the drive member 20 in order to set a fixed dose. The number of teeth in the drive member 20 over which the rotation member 21 rotates during dose setting may determine the size of the dose which is actually delivered. The dose member and the rotation member may be adapted to one another such that the rotation member may rotate only by one tooth for a fixed dose device and by more than one tooth for a variable dose device.

After the dose has been set, the dose part 16 and with it the dose member 34 is moved (pushed) by the user in the distal direction with respect to housing part 17 (opposite direction of arrow 43; second type of movement). Thus, the dose member 34 is moved in the distal direction with respect to the housing part 17. The rotation member 21 accordingly rotates in the second direction, which is opposite to the first direction, with respect to the housing (opposite direction of arrow 44). The drive member 20 follows rotational movement of the rotation member 21 in the second direction. Rotational movement of the drive member 20 in the second direction is converted into rotational movement of the piston rod 12 in the second direction, which movement, in turn, is converted into movement of the piston rod 12 in the distal direction. Accordingly, the piston 10 may be displaced in the distal direction with respect to the cartridge 4 and a dose of drug 5 is dispensed from the cartridge the amount of which corresponds to the previously set dose.

During dose delivery, the toothings 22 and 23 interlock and the ramps of the teeth 28 of the drive member 20 slide along the ramps of the teeth 27 of the stop member 26. This movement is similar to the relative rotational movement of the rotation member and the drive member described above, but for an opposite rotation direction. The stop member 26 is thereby displaced in the distal direction with respect to the drive member 20 by a distance corresponding to the depth of a tooth 27 of the stop member 26. The resilient member 31 forces the stop member 26 back into the axial start position, when the next teeth 28 of the drive member 20 are engaged by the teeth 27 of the stop member 26. A tooth of the drive member which engages the next tooth of the stop member may cause an audible and/or tactile feedback to the user.

Figure 8:
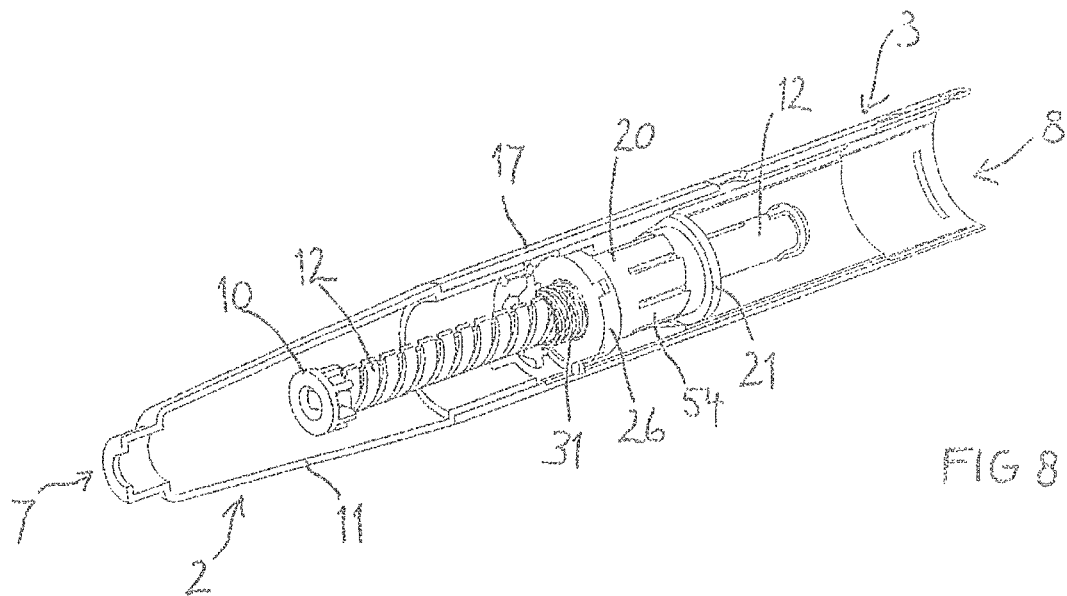
FIG. 8 shows a partial cross-section of an embodiment of a drug delivery device provided with an embodiment of the drive mechanism.

FIG. 8 shows a partial cross-section of an embodiment of a drug delivery device provided with an embodiment of the drive mechanism. A cartridge unit 2 at the distal end 7 comprises a cartridge retaining member 11. A drive unit 3 in the housing part 17 at the proximal end 8 comprises the drive member 20, the rotation member 21 and the stop member 26, which are kept in engagement by the resilient member 31. The drive unit 3 is provided to move the piston rod 12 in the distal direction in order to advance the piston 10. The drive member 20 is provided with a flexible structure, which is part of a unidirectional rotational clutch engaging the drive member 20 with the rotation member 21 and which will be designated as drive fingers 54 in the following. The central part of the drive mechanism further comprises a slider, which may have the form of a sleeve surrounding the drive member 20.

Figure 9:
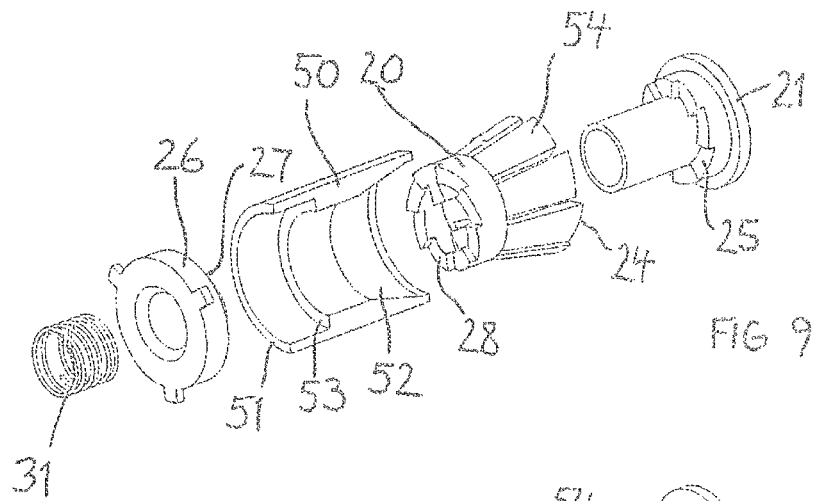
FIG. 9 shows an exploded view of a part of the drive mechanism in a state allowing a reset.
Figure 10:
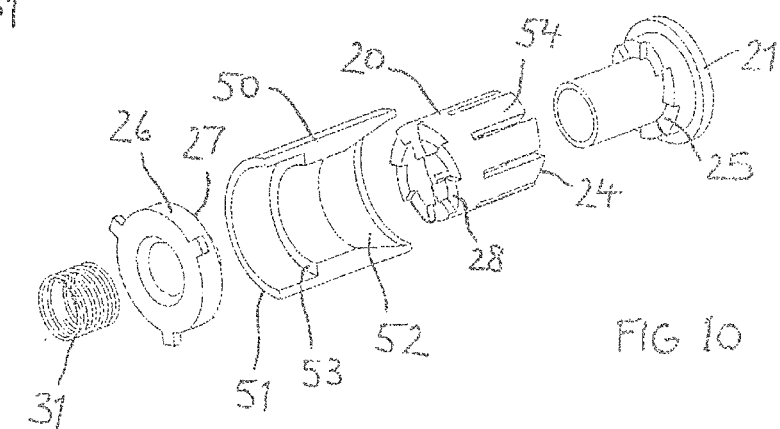
FIG. 10 shows an exploded view according to FIG. 9 in a state of normal operation.

FIGS. 9 and 10 show exploded views of the important components of the central part of an embodiment of the drive mechanism. The components are shown from left to right in the sequence of their arrangement within the drive mechanism: the resilient member 31, the stop member 26, the slider 50, the drive member 20, and the rotation member 21. In this embodiment the slider 50 may be a sleeve, which surrounds the drive member 20. The slider 50 may be provided with a coupling feature, which contacts the cartridge retaining member 11 or a part that is fastened to the cartridge retaining member 11. The coupling feature can be a coupling sleeve 51, for instance. The slider 50 is provided with a taper 52, which may be formed by an inner wall of the slider 50 and widens towards the rotation member 21, and with a contact face 53, which abuts the stop member 26. The slider 50 allows the teeth 27 of the stop member 26 and the teeth 25 of the rotation member 21 to engage the corresponding teeth 24, 28 of the drive member 20.

Figure 3:
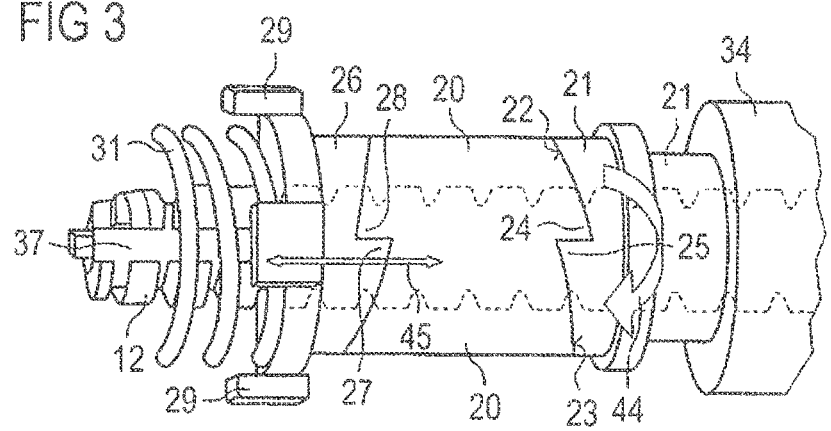
FIG. 3 shows a detail of an embodiment of the drive mechanism including a drive member.

The teeth 24 of the drive member 20 that engage the corresponding teeth 25 of the rotation member 21 are formed at end faces of drive fingers 54, which can be bent or splayed out to such an extent that they are disengaged from the teeth 25 of the rotation member 21. This is shown in FIG. 9, where the drive fingers 54 are splayed in such a manner that their ends are located on a circle, which has a larger circumference than the circle formed by the teeth of the rotation member 21. In the example shown in FIGS. 9 and 10, the teeth 24, 25 are arranged in such a manner that the rotation member 21 is rotated clockwise with respect to the housing part 17, as seen from the proximal end of the device, for setting a dose of the drug, and counter-clockwise for delivering a dose. The teeth 24, 25 may instead be arranged as shown in FIG. 3. The drive fingers 54 may be flexible or resilient in such a fashion that they tend to splay as long as they are not confined by means of the slider 50. If the cartridge retaining member 11 is attached and the drive mechanism is ready for use, the drive fingers 54 are confined by a central portion of the slider 50, which is located between the taper 52 and the contact face 53. In this state the drive member 20 may have an essentially cylindrical shape, as shown in FIG. 10. The ends of the drive fingers 54 are in contact with the teeth 25 of the rotation member 21, so that the drive member 20 and the rotation member 21 are unidirectionally rotationally coupled. The function of the slider 50 will now be described in detail in conjunction with FIGS. 11 to 14.

Figure 11:
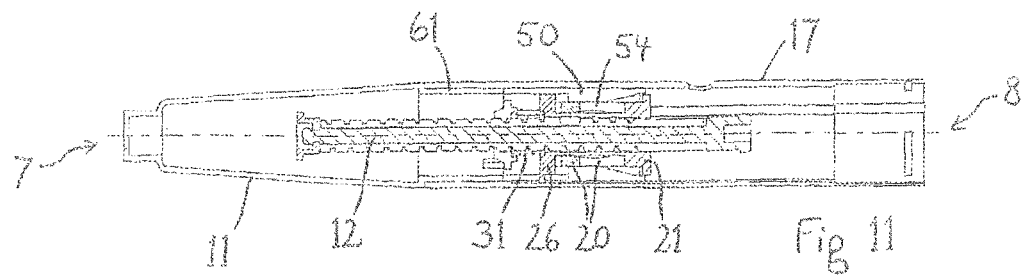
FIG. 11 shows a partial cross-section of the device of FIG. 8 in a state requiring a reset operation.

FIG. 11 shows a cross-section of the device of FIG. 8 in a state requiring a reset. The piston rod 12 has been advanced to its most distal position. The slider 50 surrounds the drive member 20 and confines the drive fingers 54 to a position where their ends engage the teeth 25 of the rotation member 21. The drive fingers 54 are maintained in this position by a central portion of the slider 50 adjacent to the taper 52. The force of the resilient member 31 keeps the stop member 26, the drive member 20 and the rotation member 21 in abutment. The slider 50 is maintained in its position by the cartridge retaining member 11, which may be provided for this purpose with an insert sleeve 61. The contact between the insert sleeve 61 and the slider 50 is facilitated by the coupling sleeve 51 of the slider 50. The stop member 26 and the rotation member 21 are both engaged with the drive member 20. In this state, the piston rod 12 cannot be reset without rotating the drive member 20, because the piston rod 12 is threadedly engaged with the housing 13 or housing part 17 and rotationally locked with the drive member 20. On the other hand, the drive member 20 is unidirectionally rotationally engaged with the stop member 26 in such a manner that a rotation of the drive member 20 is not allowed in the direction which causes the piston rod 12 to move back in the proximal direction. A reset of the piston rod 12 therefore necessitates a disengagement of the piston rod 12 from the unidirectional rotational locking. This disengagement is effected by means of the slider 50 when the cartridge unit 2 is removed.

Figure 12:
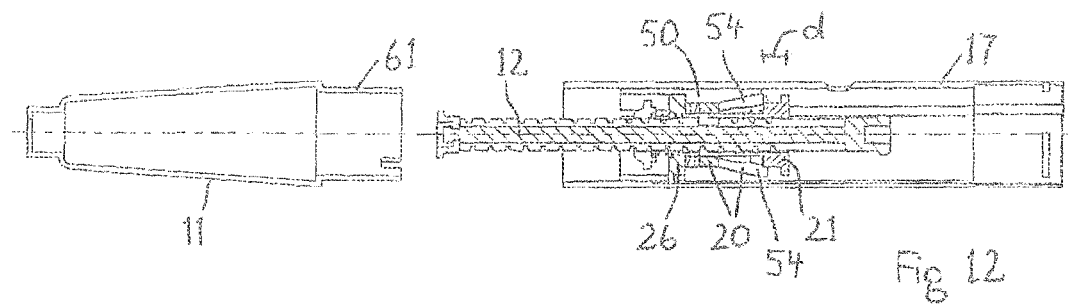
FIG. 12 shows a cross-section according to FIG. 11 after a removal of the cartridge unit and before a reset of the piston rod.

FIG. 12 shows a cross-section according to FIG. 11 after a removal of the cartridge retaining member 11, which allows the slider 50 to move in the distal direction into a location that had previously been occupied by the insert sleeve 61. The resilient force exerted by the drive fingers 54 on the taper 52 of the slider 50 moves the slider 50 a distance d in the distal direction, so that the drive fingers 54 splay and disengage from the teeth 25 of the rotation member 21. The movement of the slider 50 shifts the stop member 26 in the distal direction with respect to the drive member 20 against the force exerted by the resilient member 31. The drive member 20 is not shifted, because the splayed drive fingers 54 prevent a distal movement beyond the surface of the taper 52. The distance between the stop member 26 and the rotation member 21 is thus enlarged, and, as a consequence, the stop member 26 and the rotation member 21 are both disengaged from the drive member 20, which can now be freely rotated with respect to the housing 13 or housing part 17.

Figure 13:
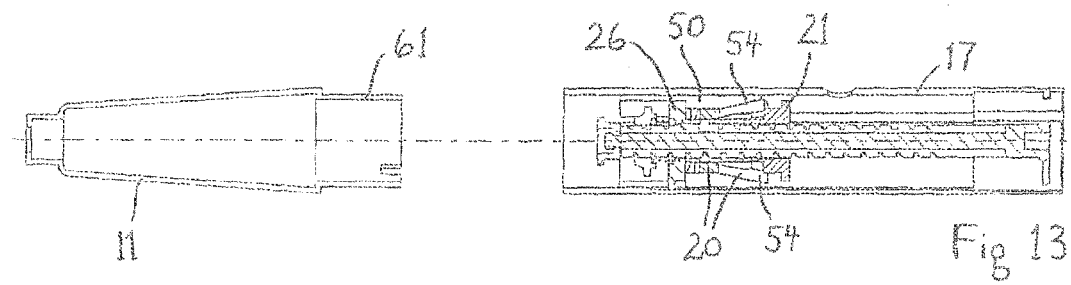
FIG. 13 shows a cross-section according to FIG. 12 after a reset of the piston rod.

FIG. 13 shows a cross-section according to FIG. 12 after a complete reset of the piston rod 12. As the cartridge retaining member 11 is removed and the slider 50 is in its most distal position, the stop member 26 and the rotation member 21 are both disengaged from the drive member 20. This allows the piston rod 12 to be rotated together with the drive member 20 and to be helically moved back in the proximal direction into its initial position, guided by the threaded coupling of the piston rod 12 to the housing 13 or housing part 17. After the reset of the piston rod 12 the cartridge retaining member 11, provided with a new cartridge, can be attached to the housing part 17 of the drive unit 3.

Figure 14:
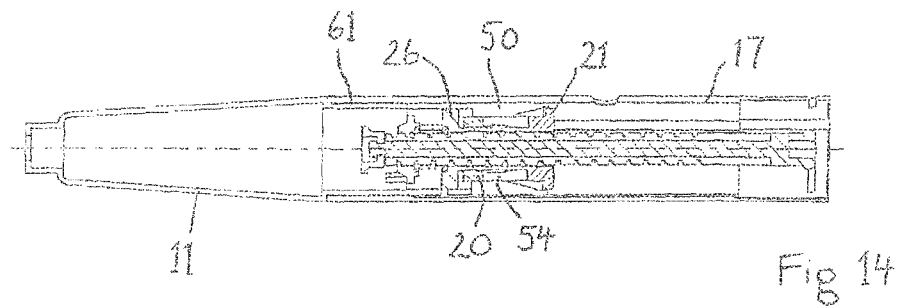
FIG. 14 shows a cross-section according to FIG. 13 with the cartridge unit attached ready for operation.

FIG. 14 shows a cross-section according to FIG. 11 with the cartridge retaining member 11 attached after the reset. The slider 50 is now in the same position as before the removal of the cartridge retaining member 11 and is kept in this position by the insert sleeve 61 pushing against the coupling sleeve 51 of the slider 50. Apart from the piston rod 12, the components of the drive mechanism are again in the same positions as shown in FIG. 11.

Although the present invention and its advantages have been described in detail, it should be understood that various changes, substitutions and alterations can be made herein without departing from the spirit and scope of the invention as defined by the appended claims.

The invention claimed is:

1. A drive mechanism for a drug delivery device, comprising: a housing,
   a drive member arranged inside the housing, the drive member being rotatable with respect to the housing,
   a piston rod, which is coupled to the drive member,
   a rotation member arranged inside the housing, the rotation member being rotatable with respect to the housing,
   drive fingers of the drive member, the drive fingers being resilient or resiliently mounted,
   a slider disposed at the drive member, the slider being axially movable between a first position, in which the slider keeps the drive fingers constrained, and a second position, in which the drive fingers are released, a first unidirectional rotational clutch engaging the drive member with the rotation member, the clutch being formed by the drive fingers when the slider is in the first position, the drive member and the rotation member being disengaged when the slider is in the second position, a unit which is attachable to the housing and removable from the housing, the drive fingers acting on the slider in such a manner that the slider is moved from the first position to the second position when the unit is being removed from the housing, a coupling sleeve of the slider, and an insert sleeve of the unit, the insert sleeve acting on the coupling sleeve and keeping the slider in the first position when the unit is attached to the housing wherein part of the slider has a taper that is operatively engaged with the drive fingers such that the drive fingers are splayed apart and disengaged from the rotation member when the slider is moved from the first position to the second position.

2. The drive mechanism of claim 1, wherein the unit comprises a cartridge retaining member.

3. The drive mechanism of claim 1, further comprising:
a stop member rotationally locked with respect to the housing or forming part of the housing, and
a second unidirectional rotational clutch engaging the stop member with the drive member when the slider is in the first position.

4. The drive mechanism of claim 3, wherein the drive member is arranged between the rotation member and the stop member.

5. The drive mechanism of claim 3, further comprising: a contact face of the slider and
a resilient member tending to hold the stop member in contact with the drive member and with the contact face of the slider and the drive member in contact with the rotation member.

6. The drive mechanism of claim 3, wherein the stop member is disengaged from the drive member when the slider is in the second position.

7. The drive mechanism of claim 1, wherein the slider surrounds the drive member, the taper is formed by an inner wall of the slider, the taper widens towards the rotation member, the drive fingers are located at an outer circumference of the drive member, and the drive member is arranged with the drive fingers extending towards the rotation member.

8. The drive mechanism of claim 1, wherein a removal of the unit allows a reset of the piston rod.

9. A drug delivery device comprising a drive mechanism according to claim 1.

10. The drug delivery device of claim 9 in the shape of a pen-type injector.

11. The drug delivery device of claim 9, wherein the drive mechanism is provided for setting and delivering a fixed dose.

* * * * *